(12) United States Patent
Katafuchi (10) Patent No.: US 9,007,073 B2
(45) Date of Patent: Apr. 14, 2015

(54) MEASURING METHOD FOR DEGREE OF DEGRADATION OF LUBRICATING OIL, AND MEASURING DEVICE THEREFOR, AS WELL AS LUBRICATING OIL MONITORING SYSTEM IN MACHINE AND DEVICE

(75) Inventor: Tadashi Katafuchi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 172 days.

(21) Appl. No.: 13/511,225

(22) PCT Filed: Nov. 22, 2010

(86) PCT No.: PCT/JP2010/070841
§ 371 (c)(1),
(2), (4) Date: May 22, 2012

(87) PCT Pub. No.: WO2011/065339
PCT Pub. Date: Jun. 3, 2011

(65) Prior Publication Data
US 2012/0229152 A1  Sep. 13, 2012

(30) Foreign Application Priority Data

Nov. 25, 2009  (JP) ................................. 2009-268117

(51) Int. Cl.
| G01R 27/26 | (2006.01) |
| G01N 27/414 | (2006.01) |
| G01N 33/28 | (2006.01) |

(52) U.S. Cl.
CPC .......... *G01N 27/414* (2013.01); *G01N 33/2876* (2013.01)

(58) Field of Classification Search
CPC ........................ G01N 33/2876; G01N 27/414

USPC .......................................................... 324/672
See application file for complete search history.

(56) References Cited

U.S. PATENT DOCUMENTS

| 5,231,358 A | * | 7/1993 | Kapsokavathis et al. ..... 324/672 |
| 5,262,732 A | * | 11/1993 | Dickert et al. ................ 324/672 |
| 5,523,692 A | * | 6/1996 | Kuroyanagi et al. ......... 324/438 |
| 5,950,147 A | * | 9/1999 | Sarangapani et al. ........ 702/179 |

(Continued)

FOREIGN PATENT DOCUMENTS

| CN | 1459630 A | 12/2003 |
| DE | 197 03 357 A1 | 8/1998 |

(Continued)

OTHER PUBLICATIONS

U.S. Appl. No. 13/510,652, filed May 18, 2012, Katafuchi.

(Continued)

*Primary Examiner* — Benjamin M Baldridge
(74) *Attorney, Agent, or Firm* — Oblon, McClelland, Maier & Neustadt, L.L.P.

(57) ABSTRACT

Provided are a method of measuring a degree of degradation of a lubricating oil and a measuring device therefor, in which (a) acidity is measured through use of an ISFET of hydrogen ion sensitive type and (b) dielectric constants or electrostatic capacitances at two or more different frequencies are obtained, to thereby determine a degradation state of the lubricating oil based on the acidity and a plurality of values of the dielectric constants or the electrostatic capacitances. Accordingly, the degree of degradation of the lubricating oil can be measured easily and precisely and a degradation mechanism of the lubricating oil can be predicted.

12 Claims, 3 Drawing Sheets

(56) References Cited

U.S. PATENT DOCUMENTS

| | | | |
|---|---|---|---|
| 6,119,074 A * | 9/2000 | Sarangapani | 702/185 |
| 6,294,133 B1 * | 9/2001 | Sawada et al. | 422/82.01 |
| 6,459,995 B1 * | 10/2002 | Collister | 702/23 |
| 7,201,051 B2 * | 4/2007 | Wang et al. | 73/291 |
| 7,297,113 B1 * | 11/2007 | Russell et al. | 600/302 |
| 8,063,644 B2 * | 11/2011 | Rezvani et al. | 324/438 |
| 8,125,224 B2 * | 2/2012 | White et al. | 324/316 |
| 8,466,521 B2 * | 6/2013 | Wey et al. | 257/414 |
| 2002/0109161 A1 * | 8/2002 | Chou et al. | 257/253 |
| 2003/0222656 A1 * | 12/2003 | Phillips et al. | 324/605 |
| 2004/0075448 A1 | 4/2004 | Lvovich et al. | |
| 2005/0109130 A1 * | 5/2005 | Ohi et al. | 73/865.6 |
| 2005/0265649 A1 * | 12/2005 | da Silva et al. | 385/13 |
| 2008/0289400 A1 | 11/2008 | Quist et al. | |
| 2009/0115416 A1 * | 5/2009 | White et al. | 324/316 |
| 2009/0216471 A1 | 8/2009 | Akiyama et al. | |
| 2009/0315574 A1 * | 12/2009 | Akiyama et al. | 324/698 |
| 2010/0007360 A1 * | 1/2010 | Kaess et al. | 324/672 |
| 2010/0052702 A1 * | 3/2010 | Ju et al. | 324/698 |
| 2010/0109686 A1 * | 5/2010 | Zhe et al. | 324/698 |
| 2010/0188073 A1 * | 7/2010 | Rothberg et al. | 324/123 R |
| 2011/0074452 A1 | 3/2011 | Katafuchi | |
| 2011/0169056 A1 * | 7/2011 | Wey et al. | 257/253 |
| 2011/0223672 A1 * | 9/2011 | Tumiatti et al. | 436/6 |
| 2013/0047708 A1 * | 2/2013 | Kim et al. | 73/53.05 |

FOREIGN PATENT DOCUMENTS

| | | | | |
|---|---|---|---|---|
| JP | 56-47614 | | 4/1981 | |
| JP | 62 162961 | | 7/1987 | |
| JP | 8-15219 A | | 1/1996 | |
| JP | 10 78402 | | 3/1998 | |
| JP | 2003 114206 | | 4/2003 | |
| JP | 2003114206 | * | 4/2003 | G01N 27/00 |
| JP | 2009 2693 | | 1/2009 | |
| JP | 2009 198341 | | 9/2009 | |
| WO | 2009 139211 | | 11/2009 | |

OTHER PUBLICATIONS

Office Action and Search Report issued Oct. 21, 2013 in China Patent Application No. 201080052096.6 (with English Translation of Categories of Cited Documents).

International Search Report Issued Feb. 8, 2011 in PCT/JP10/70841 Filed Nov. 22, 2010.

Extended European Search Report issued May 8, 2014 in Patent Application No. 10833185.1.

English Translation of Taiwanese Office Action dated Oct. 14, 2014, in Taiwanese Patent Application No. 099140779 (Taiwanese Office Action was previously submitted on Oct. 31, 2014).

* cited by examiner

MEASURING METHOD FOR DEGREE OF DEGRADATION OF LUBRICATING OIL, AND MEASURING DEVICE THEREFOR, AS WELL AS LUBRICATING OIL MONITORING SYSTEM IN MACHINE AND DEVICE

TECHNICAL FIELD

The present invention relates to a method of measuring a degree of degradation of a lubricating oil. More specifically, the present invention relates to a method of measuring a degree of degradation of a lubricating oil, which is capable of measuring a degree of degradation of a lubricating oil and predicting a degradation mechanism, and to a measuring device therefor and a lubricating oil monitoring system for a machine and a device.

BACKGROUND ART

The degree of degradation of a lubricating oil has large effects on the performance and durability of a machine and a device that use the lubricating oil, and on the performance of energy saving. Further, the progression speed of degradation of the lubricating oil varies considerably depending upon the condition under which the lubricating oil is used. Therefore, it is necessary that the degradation state of the lubricating oil can be measured easily and precisely.

Conventionally, in order to measure the degree of degradation of the lubricating oil such as an engine oil, there have been used a method in which an operating time of the lubricating oil is used as a measure and a method in which properties (e.g., a kinetic viscosity, an insoluble content, an acid number, a base number) of the lubricating oil are measured and a degree of degradation is determined based on the measurement result. However, those methods cannot measure a degree of degradation of the lubricating oil easily and precisely.

In order to solve the above-mentioned problem, for example, Patent Document 1 discloses a method in which a resistance sensor is installed in an oil pan and the lifetime of the lubricating oil is measured based on a change in electric resistance of an engine oil. Further, there are also disclosed a large number of methods in which a pH sensor is installed in an oil pan and the lifetime of the lubricating oil is measured based on a change in pH involved in a change in acidity and basicity of an oil.

Those methods are simple because a change in electric resistance and a change in pH in the lubricating oil can be checked on a steady basis, and it can be determined that the lifetime has expired at a time when a change rate of the electric resistance or pH has reached a predetermined value or state.

However, the electric resistance also fluctuates due to the contamination of soot (carbon), which is not a polar substance generated along with the degradation of the lubricating oil, and hence, the degree of degradation of the lubricating oil may not be measured precisely. Further, even if the pH indicates the degree of degradation, a clue for determining a cause of degradation (degradation mechanism) that has degraded the lubricating oil cannot be obtained from the pH. Thus, there is a problem in terms of the management of degradation of the lubricating oil.

In recent years, a research is being conducted for measuring a degree of degradation of the lubricating oil by measuring an impedance of the lubricating oil and also for clarifying the influence of the contamination of soot.

For example, in Non-Patent Document 1, an impedance of the lubricating oil in a wide frequency range of 20 Hz to 600 kHz is measured, and a change in impedance caused by the contamination of soot or diesel is studied with the impedance being divided into a resistance (resistance component) and a reactance (capacitance component). However, the study result has not clearly found out a relationship between the concentration of soot or diesel and the impedance.

Patent Document 2 discloses a device for measuring a complex impedance of an oil, obtaining an electric conductivity with the assumption that a real part of an inverse number of the complex impedance is a resistance component, obtaining a dielectric constant with the assumption that an imaginary part of the inverse number of the complex impedance is a capacitance component, and detecting degradation in an oil from the electric conductivity and the dielectric constant.

However, according to the method described in Patent Document 2, it is difficult to measure a degree of degradation from a measured value of a dielectric constant precisely and analyze a degradation mechanism (cause of degradation) of the lubricating oil.

Further, there is also a problem in that the device for measuring an impedance disclosed in Non-Patent Document 1 and Patent Document 2 has a complicated measurement circuit, which results in high cost of the device.

BACKGROUND ART

Patent Document

[Patent Document 1] JP 10-78402 A
[Patent Document 2] JP 2009-2693 A

Non-Patent Document

[Non-Patent Document 1] Sensors and Actuators, B127 (2007), 613-818

SUMMARY OF THE INVENTION

Problem to be solved by the Invention

Under such circumstances, it is an object of the present invention to provide a method of measuring a degree of degradation of a lubricating oil, which is capable of measuring a degree of degradation of the lubricating oil easily and precisely and predicting a degradation mechanism of the lubricating oil, and also provide a measuring device therefor and a lubricating oil monitoring system for a machine and a device, which uses the device for measuring a degree of degradation of a lubricating oil.

Means for Solving the Problem

The inventors of the present invention earnestly studied so as to achieve the above-mentioned object, and consequently, found that acidity of a lubricating oil changes depending upon an amount of a polar substance generated due to the degradation of the lubricating oil and that a rate of a change in dielectric constants or electrostatic capacitances of the lubricating oil at two or more different frequencies provides information on a degradation mechanism (cause of degradation) of the lubricating oil. The present invention has been achieved based on such findings.

That is, the present invention provides:

[1] a method of measuring a degree of degradation of a lubricating oil, including (a) measuring acidity through use of an ISFET of hydrogen ion sensitive type and (b) obtaining dielectric constants or electrostatic capacitances at two or more different frequencies, to thereby determine a degradation state of the lubricating oil based on the acidity and a plurality of values of the dielectric constants or the electrostatic capacitances;

[2] the method of measuring a degree of degradation of a lubricating oil according to the above-mentioned item [1], further including determining that the lubricating oil has been degraded when the acidity measured through use of the ISFET of hydrogen ion sensitive type in the step (a) has reached a set value, and predicting a degradation mechanism of the lubricating oil based on a rate of a change in dielectric constant or electrostatic capacitance with respect to a frequency between the two or more different frequencies, the rate being obtained from the dielectric constants or the electrostatic capacitances at the two or more different frequencies in the step (b);

[3] the method of measuring a degree of degradation of a lubricating oil according to the above-mentioned item [1] or [2], in which the step (a) of measuring acidity through use of the ISFET of hydrogen ion sensitive type includes a step of applying a constant voltage between a drain and a source of the ISFET of hydrogen ion sensitive type and measuring a current flowing between the drain and the source or a step of applying a constant current to flow between the drain and the source and measuring a voltage between the drain and the source;

[4] the method of measuring a degree of degradation of a lubricating oil according to the above-mentioned item [3], in which the step (a) of measuring acidity through use of the ISFET of hydrogen ion sensitive type includes a step of applying different voltages between the drain and the source and measuring a difference of currents between the drain and the source at respective voltage values or a step of applying different currents to flow between the drain and the source and measuring a difference of voltages between the drain and the source at respective current values;

[5] the method of measuring a degree of degradation of a lubricating oil according to any one of the above-mentioned items [1] to [4], in which at least one frequency ($H_1$) of the two or more different frequencies in the step (b) is 100 Hz or less, and another frequency ($H_2$) is more than ($H_1$) and 10,000 Hz or less;

[6] the method of measuring a degree of degradation of a lubricating oil according to the above-mentioned item [5], further including obtaining a dielectric constant ($\in_1$) or an electrostatic capacitance ($C_1$) at the frequency ($H_1$) and a dielectric constant ($\in_2$) or an electrostatic capacitance ($C_2$) at the frequency ($H_2$) and determining a degradation state of the lubricating oil based on a rate of a change in dielectric constant with respect to the frequency $[(\in_1-\in_2)(H_2-H_1)]$ or a rate of a change in electrostatic capacitance with respect to the frequency $[(C_1-C_2)(H_2-H_1)]$;

[7] a device for measuring a degree of degradation of a lubricating oil, including: (A) an acidity measuring part including an ISFET of hydrogen ion sensitive type and a circuit for applying a constant voltage between a drain and a source of the ISFET of hydrogen ion sensitive type and measuring a current flowing between the drain and the source or a circuit for applying a constant current to flow between the drain and the source and measuring a voltage between the drain and the source; and (B) an electrostatic capacitance measuring part including a pair of electrodes, an AC power source for applying an AC voltage between the pair of electrodes under control of a frequency to a region of 100 Hz or less, and an electrostatic capacitance measuring circuit for measuring an electrostatic capacitance between the pair of electrodes;

[8] the device for measuring a degree of degradation of a lubricating oil according to the above-mentioned item [7], further including a dielectric constant calculating part including a dielectric constant calculating circuit for calculating a dielectric constant based on an electrostatic capacitance measured value obtained in the electrostatic capacitance measuring part; and

[9] a lubricating oil monitoring system for a machine and a device, including the device for measuring a degree of degradation of a lubricating oil according to the above-mentioned item [7] or [8]

Effects of the Invention

According to the present invention, it is possible to provide a method of measuring a degree of degradation of a lubricating oil, which is capable of measuring a degree of degradation of the lubricating oil easily and precisely and predicting a degradation mechanism of the lubricating oil, and also provide a device for measuring a degree of degradation of a lubricating oil and a lubricating oil monitoring system for a machine and a device, which uses the device for measuring a degree of degradation of a lubricating oil.

MODE FOR CARRYING OUT THE INVENTION

The present invention is a method of measuring a degree of degradation of a lubricating oil and a device for measuring a degree of degradation of a lubricating oil, in which (a) acidity is measured through use of an ISFET of hydrogen ion sensitive type (hereinafter, sometimes referred to as "pH-ISFET") and (b) dielectric constants or electrostatic capacitances at two or more different frequencies are measured, to thereby determine a degradation state of the lubricating oil based on the acidity and values of a plurality of the dielectric constants or the electrostatic capacitances.

Determining a degradation state in the present invention refers to measuring a degree of degradation and predicting a degradation mechanism (cause of degradation). Through both the measurement and the prediction, the lifetime of a lubricating oil in use can be predicted precisely and the lubrication management can be performed appropriately.

The term "acidity" in the present invention refers to an index measured through use of a pH-ISFET, indicating a rate of a change in voltage value or current value of a sample lubricating oil with reference to a difference (change amount) in voltage value or current value between a new oil and a degraded oil (lubricating oil whose lifetime has expired).

[(a) A Method of Measuring Acidity Through Use of a Ph-ISFET and a Measuring Device Therefor]

An ion sensitive field effect transistor (ISFET) of hydrogen ion sensitive type is used for measurement of a degree of degradation of a lubricating oil of the present invention.

The pH-ISFET is the one that is generally used, in which two N-type semiconductor islands (source and drain) are produced on a P-type substrate and a gate made of an insulating film is provided, and examples of the material for the gate include tantalum oxide ($Ta_2O_5$) and silicon nitride ($Si_3N_4$).

Figure 1:
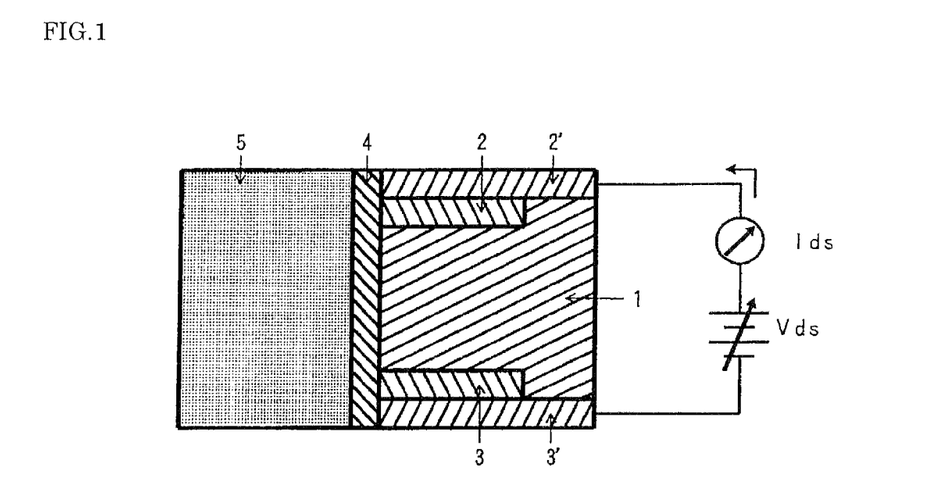
[FIG. 1] A schematic diagram illustrating one example of an ISFET of hydrogen ion sensitive type used in a method of measuring a degree of degradation of a lubricating oil of the present invention.
Figure 2:
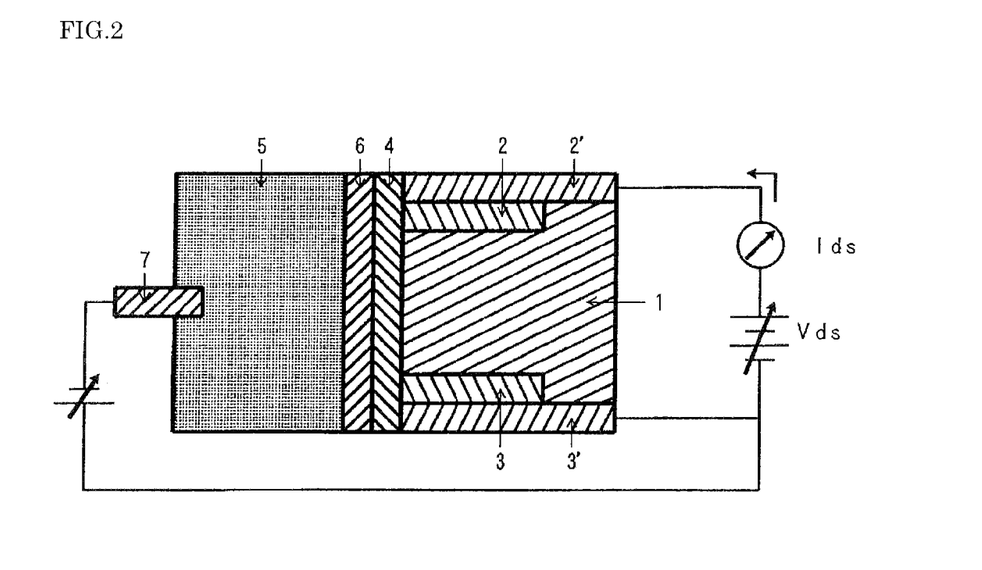
[FIG. 2] A schematic diagram illustrating another example of the ISFET of hydrogen ion sensitive type used in the method of measuring a degree of degradation of a lubricating oil of the present invention.

FIG. 1 is a schematic diagram illustrating one example of the pH-ISFET used in the method of measuring a degree of degradation of a lubricating oil of the present invention, and FIG. 2 is a schematic diagram illustrating another example of the pH-ISFET used in the method of measuring a degree of degradation of the present invention. Hereinafter, a method of measuring acidity of a lubricating oil through use of a pH-ISFET and a measuring device therefor are described with reference to FIGS. 1 and 2.

Referring to FIGS. 1 and 2, at both ends of a P-type semiconductor 1, there are formed two N-type semiconductor islands, that is, a drain 2 and a source 3, and wirings are connected to a drain electrode 2' and a source electrode 3', which are in contact with the respective islands. On one side of the P-type semiconductor 1 having the drain 2 and the source 3 formed therein, a gate 4 is formed, the surface of which is in contact with a lubricating oil 5.

When hydrogen ions of the lubricating oil 5 have accumulated around the gate 4, free holes, which are majority carriers of the P-type semiconductor 1, move away from the gate 4 due to repulsion. On the other hand, electrons existing as minority carriers in the P-type semiconductor 1 are attracted to the gate 4, thereby forming an N-channel. As a result, a current flows between the drain 2 and the source 3.

It should be noted that, in the example illustrated in FIG. 2, a hydrogen ion permeable membrane 6 is provided on the gate 4 on the lubricating oil 5 side, but the hydrogen ion permeable membrane 6 is not essential for carrying out the present invention because the principle is that the ISFET measures a potential of the gate.

As the concentration of the hydrogen ions in the lubricating oil 5 becomes higher, the N-channel becomes thicker, which causes a larger current to flow between the drain 2 and the source 3. Accordingly, in a case where a voltage applied between the drain 2 and the source 3 (Vds) is kept constant, a current flowing between the drain 2 and the source 3 (Ids) becomes larger as the concentration of the hydrogen ions in the lubricating oil 5 becomes higher. On the other hand, in a case where the current caused to flow between the drain 2 and the source 3 (Ids) is kept constant, the voltage between the drain 2 and the source 3 (Vds) becomes smaller as the concentration of the hydrogen ions in the lubricating oil 5 becomes higher.

By measuring such a current value that is obtained in the case where a constant voltage is applied between the drain 2 and the source 3 described above or by measuring such a voltage value that is obtained in the case where a constant current is applied to flow therebetween, it becomes possible to make a determination as to the concentration of the hydrogen ions in the lubricating oil, that is, the degree of degradation. If such current value or voltage value is measured over a long period of time, the progress of degradation may be understood.

As in usual cases, the pH-ISFET may be provided with a reference electrode 7 for use, as illustrated in the example of FIG. 2. However, the pH-ISFET may be used without being provided with the reference electrode 7. This case is more preferred because the circuit is simpler and management of the reference electrode is not required.

It should be noted that, though not illustrated, an acidity measuring part in the device for measuring a degree of degradation of a lubricating oil is immersed into the lubricating oil in actual use so that the gate 4 (hydrogen ion permeable membrane 6 in the example of FIG. 2) is brought into contact with the lubricating oil 5, and thus needs to have a structure that allows such use. In addition, between the drain 2 and the source 3, there is connected a measurement circuit for measuring a current value in a case where a constant voltage is applied by a constant voltage device, or a measurement circuit for measuring a voltage value in a case where a constant current is caused to flow by a constant current device.

In a case where acidity is measured through use of the above-mentioned pH-ISFET, immediately after the measurement is started by applying a constant voltage or by causing a constant current to flow, the measured value is not stable with a tendency that the current value Ids increases gradually in the case where the constant voltage is applied or a tendency that the voltage value Vds decreases gradually in the case where the constant current is caused to flow. In both the cases, the measured value gradually settles into a constant value. Accordingly, a measurement time period is preferably set to 5 seconds or longer, particularly, 10 seconds or longer.

Further, with only one measurement, only an initial output is measured and a measured value is unlikely to be stable. Therefore, it is preferred to perform a plurality of measurements by providing a time for applying a voltage different from that of the first measurement or a measurement time for causing a current different from that of the first measurement to flow. Further, the preferred conditions under which the measured value converges are within 10 seconds of a measurement time at the different voltage or current at five or more measurements.

As a method of obtaining acidity from a voltage value or a current value thus measured, the following method is preferred.

In the case where the measured value is a voltage value, a voltage value ($v_O$) of a new oil and a voltage value ($v_E$) of a degraded oil (oil whose lifetime has expired) are measured previously by a preliminary experiment, and acidity (acidity index) is calculated from a voltage value ($v_X$) of a sample lubricating oil by the following Expression (I).

$$\text{Acidity index} = [[(v_O) - (v_X)]/[(v_O) - (v_E)]] \times 10 \tag{I}$$

Herein, the acidity of the sample lubricating oil is indicated by an index with the acidity of the new oil being 0 and the acidity of the degraded oil being 10, but the acidity of the sample lubricating oil may be calculated with the acidity of the degraded oil being 100. That is, the "set value" in the present invention refers to 10 or 100 in the above-mentioned case.

Further, the degraded oil is the one that has reached the end of the lifetime and should be renewed from the viewpoint of lubrication management, and can be set by appropriate selection. Further, even in the case where the measured value is a current value, acidity can be obtained by a method pursuant to the case where the measured value is a voltage value.

[(b) A Method of Measuring Dielectric Constants and Electrostatic Capacitances at Two or More Different Frequencies and a Measuring Device Therefor]

In the present invention, dielectric constants or electrostatic capacitances at two or more different frequencies are measured, to thereby determine the degradation state of a lubricating oil based on the values of the dielectric constants or the electrostatic capacitances. Thus, it is necessary to obtain the dielectric constants or the electrostatic capacitances at two or more different frequencies.

It should be noted that the term "two or more" in the above-mentioned description includes the case of "two" and the case of "three or more", and there is no particular constraint on the upper limit of the number of measurements. More specifically, electrostatic capacitances $C_1, C_2, \ldots C_n$ at frequencies $H_1, H_2, \ldots H_n$ are measured, and dielectric constants $\in_1, \in_2, \ldots \in_n$ are obtained based on the measured electrostatic capacitances.

If dielectric constants or electrostatic capacitances of a lubricating oil at two or more different frequencies can be measured, a rate of a change in dielectric constant or electrostatic capacitance with respect to a change in frequency can be measured, and the degradation state of a lubricating oil can be obtained as described later. Further, in the case of three or more different frequencies, a change in dielectric constant or electrostatic capacitance with respect to a frequency can be grasped more widely and precisely.

It is preferred that at least one frequency (generally, the lowest frequency) ($H_1$) of the two or more different frequencies be 100 Hz or less. If the frequency ($H_1$) is 100 Hz or less, the dielectric constant or the electrostatic capacitance greatly changes depending upon the concentration of a polar substance generated due to the degradation of a lubricating oil, and hence, the degradation states of lubricating oils can be discriminated and determined precisely. Thus, the frequency ($H_1$) is preferably 80 Hz or less, more preferably 60 Hz or less.

Although there is no particular constraint on the lower limit of the frequency ($H_1$) of 100 Hz or less, the lower limit is preferably 1 Hz or more, more preferably 5 Hz or more, still more preferably 10 Hz or more because, at an extremely low frequency, there is a fear that the value of a dielectric constant or an electrostatic capacitance to be measured may not be stable, which makes it necessary to take a considerable time for measurement, and a measured value having reproducibility may not be obtained due to a large amount of noise.

Further, based on the above-mentioned description, at least one frequency ($H_1$) of the two or more different frequencies is preferably in a range of 5 to 80 Hz, more preferably in a range of 10 to 60 Hz.

On the other hand, the frequency ($H_2$) other than the frequency ($H_1$) is larger than the frequency ($H_1$), and is preferably 10,000 Hz or less. If the frequency is 10,000 Hz or less, the dielectric constant or the electrostatic capacitance sufficiently changes depending upon the concentration of a polar substance generated due to the degradation of a lubricating oil, and hence, the degradation states of lubricating oils can be discriminated and determined precisely. The upper limit of the frequency ($H_2$) is preferably less than 10,000 Hz, more preferably 1,000 Hz or less, still more preferably 500 Hz or less, particularly preferably 200 Hz or less.

The range of frequencies ($H_3$) . . . ($H_n$) in the case of measuring dielectric constants and the like at three or more different frequencies may be selected in a range of more than ($H_2$) and 10,000 Hz or less, preferably 1,000 Hz or less.

If the values of dielectric constants or electrostatic capacitances at two or more different frequencies obtained under the above-mentioned preferred conditions are larger than those of a new oil, for example, it is determined that the lubricating oil is degraded.

Next, a method of predicting a degradation mechanism (cause of degradation) of a lubricating oil based on values of dielectric constants or electrostatic capacitances at two or more different frequencies is described.

As a method of predicting a degradation mechanism (cause of degradation) of a lubricating oil based on values of dielectric constants or electrostatic capacitances at two or more different frequencies, there is a method of predicting the degradation state of a lubricating oil based on a rate (magnitude) of a change in dielectric constant or electrostatic capacitance with respect to a frequency.

Specifically, for example, a rate of a change in dielectric constant with respect to a frequency $[(\in_1-\in_2)/(H_2-H_1)]$ or a rate of a change in electrostatic capacitance $[(C_1-C_2)/(H_2-H_1)]$ is considered.

In the case where $[(\in_1-\in_2)/(H_2-H_1)]$ or $[(C_1-C_2)/(H_2-H_1)]$ is considerably larger than the normal value (exceeds 200% compared with the normal value), it is presumed that, in addition to a polar substance generated due to the degradation of a lubricating oil, a polar substance generated due to other factors has been mixed (Degradation state I). It has been confirmed that such a degradation mechanism is found in a gasoline engine oil used in a gasoline engine.

In contrast, in the case where $[(\in_1-\in_2)/(H_2-H_1)]$ or $[(C_1-C_2)/(H_2-H_1)]$ is slightly larger than the normal value (within 200% of the normal value) but the acidity is so high that the degradation of a lubricating oil is recognized, it is presumed that another non-polar substance or weakly polar substance has been mixed as well as an increase of a polar substance generated due to the degradation of a lubricating oil (Degradation state II). Degradation caused by such a degradation mechanism is recognized in the case where soot has been mixed in a diesel engine oil used in a diesel engine. In such a case, it is necessary to adjust the burning state in an engine and to take measures including the improvement of a soot trapping device.

The criterion for determining whether or not a rate of a change in dielectric constant or electrostatic capacitance with respect to a frequency is large may be set by performing a preliminary experiment of comparing calculated values regarding engine oils under different kinds of specifications before and after an engine test. In such a case, it is preferred that a viscometer or a hue meter be provided in a measuring device.

Thus, the degradation mechanism of a lubricating oil can be predicted.

Next, a measuring device preferred for measuring a dielectric constant or an electrostatic capacitance in the present invention is described.

Figure 3:
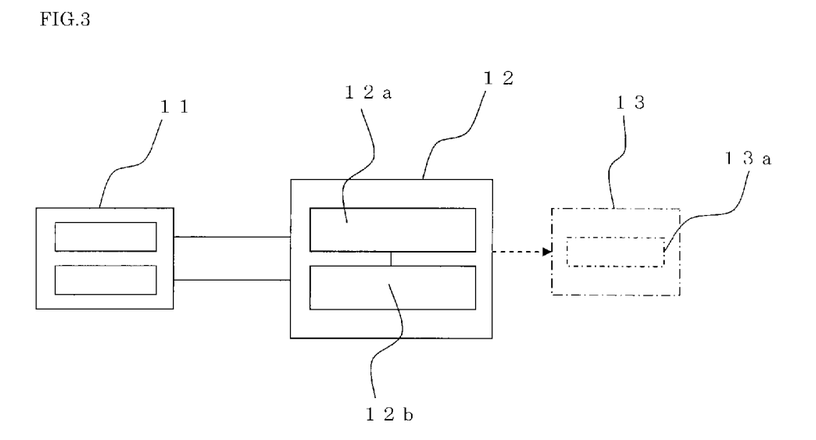
[FIG. 3] A conceptual diagram illustrating one example of a device for measuring a degree of degradation of a lubricating oil of the present invention (electrostatic capacitance measuring part and dielectric constant calculating part).

FIG. 3 is a conceptual diagram illustrating one example of an electrostatic capacitance measuring part and a dielectric constant calculating part in the device for measuring a degree of degradation of a lubricating oil used in the method of measuring a degree of degradation of a lubricating oil of the present invention.

The device for measuring a degree of degradation of a lubricating oil includes a pair of electrodes 11 and an electrostatic capacitance measuring part 12 having an AC power source 12a for applying an AC voltage between the pair of electrodes, which is capable of controlling the frequency to a region of 100 Hz or less, and an electrostatic capacitance measuring circuit 12b for measuring an electrostatic capacitance between the pair of electrodes. The measuring device may further include a dielectric constant calculating part 13 having a dielectric constant calculating circuit 13a for calculating a dielectric constant based on an electrostatic capacitance measured value obtained in the electrostatic capacitance measuring part 12.

It is preferred that the AC power source 12a be capable of controlling the frequency to a region of 10 Hz or less, and it is more preferred that the AC power source 12a be capable of controlling the frequency to 1 Hz.

According to a method of measuring an electrostatic capacitance of a lubricating oil and a method of calculating a dielectric constant thereof, first, the pair of electrodes 11 are soaked in a lubricating oil, an AC voltage of an intended frequency ($H_1$) is applied between the electrodes by the AC power source 12a of the electrostatic capacitance measuring part 12, and an electrostatic capacitance $C_1$ between the electrodes is measured by the electrostatic capacitance calculating circuit 12b. Then, if required, a dielectric constant $\in_1$ is calculated from the electrostatic capacitance $C_1$ by the dielectric constant calculating circuit 13a. Similarly, an electrostatic capacitance $C_2$ at a different frequency ($H_2$) is measured, and similarly, a dielectric constant $\in_2$ is calculated. It should be noted that the dielectric constant $\in$ and the electrostatic capacitance C have a relationship of the following Expression (II) . Thus, an electrostatic capacitance is to be measured as a condition for obtaining a dielectric constant.

$$\in = C \times d/s \tag{II}$$

(where d represents a distance between the pair of electrodes, and s represents a surface area of the electrode.)

Further, it is preferred that the measured voltage in the above-mentioned electrostatic capacitance measurement be set in a range of 0.1 to 10 $V_{p\text{-}p}$.

As the pair of electrodes 11 in FIG. 3, comb-shaped electrodes are preferred, and comb-shaped minute electrodes are particularly preferred. Further, as the electrostatic capacitance measuring part 12 and the dielectric constant calculating part 13, an LCR meter or a C meter can be used.

According to the method of measuring the electrostatic capacitance C of a lubricating oil directly and obtaining the dielectric constant $\in$ from the value of the electrostatic capacitance C as described above, the device is simple and an electrostatic capacitance and a dielectric constant of a lubricating oil can be measured and calculated easily at low cost with high precision.

Particularly, in the case where comb-shaped electrodes are used as the pair of electrodes 11, there is an effect that an evaluation device can be miniaturized, and the degree of degradation of a lubricating oil can be measured only by extracting a trace amount of a sample oil (lubricating oil). Simultaneously, because it is easy to observe the sample oil in measurement, there is also an effect that supplementary information on a degree of degradation of a lubricating oil and a degradation mechanism can be obtained from the external appearance (color, etc.) and odor of the sample oil.

Figure 4:
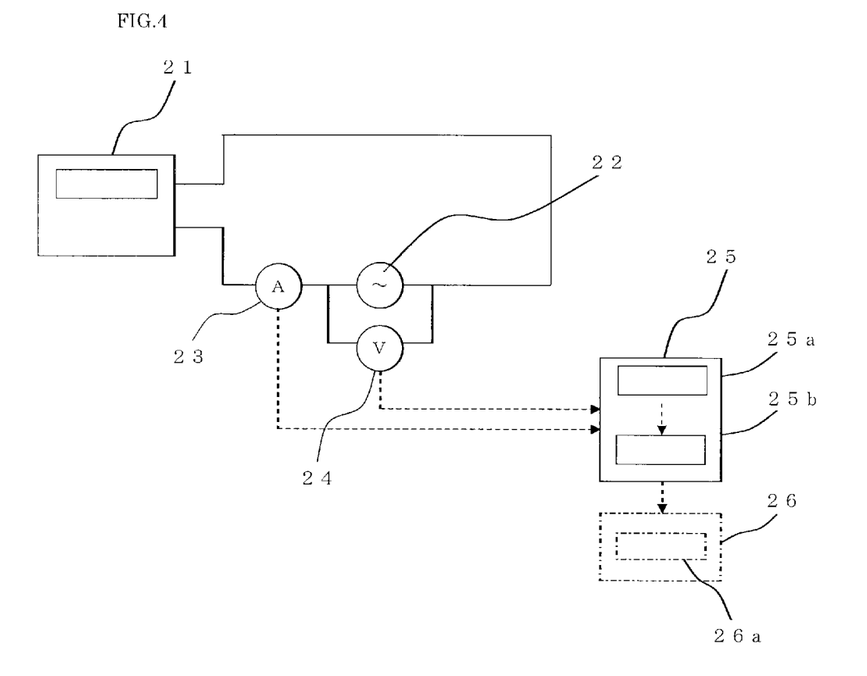
[FIG. 4] A conceptual diagram illustrating another example of the device for measuring a degree of degradation of a lubricating oil of the present invention (electrostatic capacitance measuring part and dielectric constant calculating part).

FIG. 4 is a conceptual diagram illustrating another example of the device for measuring a degree of degradation of a lubricating oil (electrostatic capacitance measuring part and dielectric constant calculating part) used for carrying out the method of measuring a degree of degradation of a lubricating oil of the present invention.

This measuring device is a device for measuring a degree of degradation of a lubricating oil, including a pair of electrodes 21, an AC power source 22 capable of controlling a frequency to a region of 100 Hz or less, an ammeter 23, a voltmeter 24, and an electrostatic capacitance measuring part 25 having a complex impedance calculating circuit 25a and an electrostatic capacitance calculating circuit 25b. The measuring device may further include a dielectric constant calculating part 26 having a dielectric constant calculating circuit 26a.

According to a method of measuring and calculating an electrostatic capacitance or a dielectric constant, first, the pair of electrodes 21 are soaked in a lubricating oil, and an AC voltage of a frequency $H_1$ is applied between the electrodes by the AC power source 22 capable of controlling the frequency to a region of 100 Hz or less . Then, an impedance Z (complex impedance) of a lubricating oil is calculated from a current I and a voltage V measured by the ammeter and the voltmeter and a phase difference between the current and the voltage . Then, from a value of an imaginary part (reactance) $Z_C$ of a real part (resistance component) $Z_R$ and the imaginary part (reactance) $Z_C$ constituting the impedance, a capacitance component (that is, an electrostatic capacitance) $C_1$ is calculated (see the following Expression (III)) . Then, if required, a dielectric constant $\in_1$ is obtained from a value of the electrostatic capacitance $C_1$. Further, similarly, an electrostatic capacitance $C_2$ at a different frequency $H_2$ is measured.

$$\begin{aligned} Z &= V/I \\ &= Z_R + Z_C \\ &= R + 1/j\omega C \end{aligned} \tag{III}$$

(where Z represents an impedance, $Z_R$ represents a resistance component, $Z_C$ represents an imaginary part of the impedance, R represents a resistance, j represents an imaginary unit, ω represents an AC angular frequency, and C represents an electrostatic capacitance.)

It is preferred that the measured voltage in the above-mentioned electrostatic capacitance measurement be set in a range of 0.1 to 10 $V_{p\text{-}p}$.

As the device for measuring a degree of degradation of a lubricating oil of the present invention, any measuring device may be used as long as the measurement of acidity through use of the pH-ISFET and the measurement of an electrostatic capacitance or the calculation of a dielectric constant at two or more different frequencies can be performed. However, it is preferred to use a device in which both (the acidity measuring part and the electrostatic capacitance measuring part (further, the dielectric constant calculating part)) are integrated.

For example, it is preferred that the device for measuring a degree of degradation of a lubricating oil of the present invention include (A) an acidity measuring part having a pH-ISFET and a circuit for applying a constant voltage between a drain and a source of the pH-ISFET and measuring a current flowing between the drain and the source or a circuit for causing a constant current to flow between the drain and the source and measuring a voltage between the drain and the source, and (B) an electrostatic capacitance measuring part having a pair of electrodes, an AC power source for applying an AC voltage between the pair of electrodes under control of the frequency to a region of 100 Hz or less, and an electrostatic capacitance measuring circuit for measuring an electrostatic capacitance between the electrodes. It is more preferred that the device for measuring a degree of degradation of a lubricating oil of the present invention further include (C) a dielectric constant calculating part having a dielectric constant calculating circuit for calculating a dielectric constant based on a value of the electrostatic capacitance obtained in the electrostatic capacitance measuring part.

The above-mentioned device for measuring a degree of degradation of a lubricating oil of the present invention can be incorporated in a part of an operation monitoring system of a machine and a device such as an engine so as to determine the state of a lubricating oil. Thus, the device for measuring a degree of degradation of a lubricating oil of the present invention can be used as a lubricating oil monitoring system for a machine and a device.

EXAMPLES

Examples of the present invention are described further, but the present invention is not limited by these examples.

Example

Figure 5:
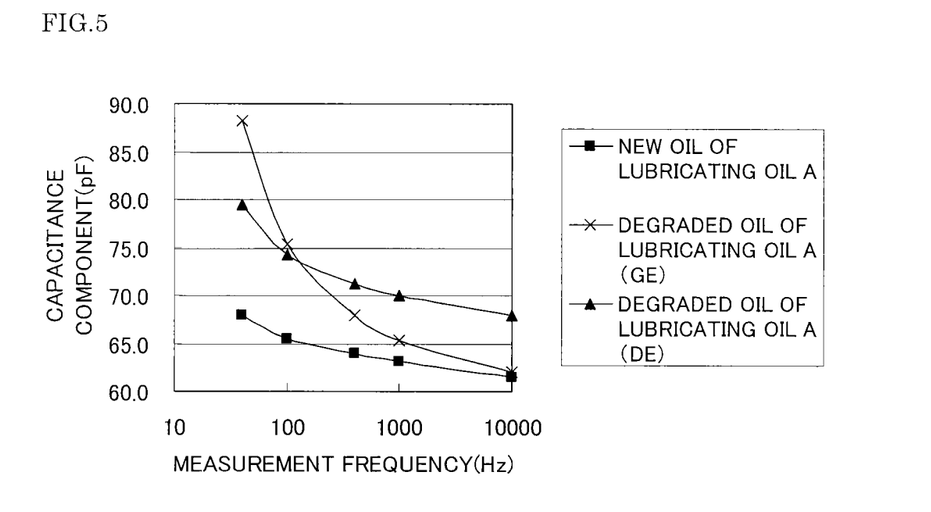
[FIG. 5] A diagram (graph) showing a relationship between the capacitance component (electrostatic capacitance) of a lubricating oil used in an example and the frequency.

The acidity and capacitance component (electrostatic capacitance) of lubricating oils of the following sample oils (i) to (iii) were measured.
(Sample Oils)
 (i) New oil of lubricating oil A (ashless engine oil)
 (ii) Degraded oil (GE) of lubricating oil A (ashless engine oil) [used in gasoline engine (GE) to be degraded: mixed with a polar substance]
 (iii) Degraded oil (DE) of lubricating oil A (ashless engine oil) [used in diesel engine (DE) to be degraded: mixed with soot]
 (1) Measurement of Acidity
Regarding the above-mentioned sample oils (i) to (iii), with the use of the device illustrated in FIG. 1, a constant current of 0.5 mA was applied to flow between the drain 2 and the source 3, and a voltage (Vds) between the drain 2 and the source 3 was measured on constant time intervals. In the measurement, a non-measurement time was set to be 2 seconds, and a voltage was measured 18 seconds after the start of the measurement (after the constant current started to flow). The measurement operation was repeated 10 times, and a convergence value of the measured voltage values was determined as a measured value of the drain-source voltage (Vds) at that time point. Further, the acidity (acidity index) was obtained from the voltage value by the above-mentioned Expression (I). Table 1 shows the results.
(2) Measurement of an electrostatic capacitance and the calculation of a dielectric constant
Regarding the sample oils (i) to (iii), with the use of the device for measuring a degree of degradation of a lubricating oil (the electrostatic capacitance measuring part and the dielectric constant calculating part) illustrated in FIG. 4, capacitance components (electrostatic capacitances) of a complex impedance at frequencies of 40, 100, 150, 1,000, and 10,000 Hz were measured under the following measurement conditions.
(Measurement Conditions)
 Electrodes: comb-shaped minute electrodes
 Measured voltage: 1 $V_{p\text{-}p}$
FIG. 5 shows the results as a change in capacitance component (electrostatic capacitance) with respect to a frequency. Further, assuming that the capacitance components (electrostatic capacitances) at the frequencies of 40 Hz and 100 Hz are $C_{40}$ (pF) and $C_{100}$ (pF), a rate of a change in capacitance component with respect to a frequency was calculated by the following expression.

Rate of change in capacitance component (electrostatic capacitance) with respect to frequency (%)

$$=[(C_{40}-C_{100})/(100-40)]\times 100$$

Similarly, assuming that dielectric constants obtained from the capacitance components at the frequencies of 40 Hz and 100 Hz are $E_{40}$ and $\in_{100}$, a rate of a change in dielectric constant with respect to a frequency can be calculated by the following expression.

Rate of change in dielectric constant with respect to frequency (%)

$$=[(\in_{40}-\in_{100})/(100-40)]\times 100$$

Herein, Table 1 shows the results of the rate of a change in capacitance component with respect to a frequency.

TABLE 1

| | | SAMPLE OIL (i) (NEW OIL) | SAMPLE OIL (ii) (DE-GRADED OIL (GE)) | SAMPLE OIL (iii) (DE-GRADED OIL (DE)) |
|---|---|---|---|---|
| ACIDITY | DRAIN-SOURCE VOLTAGE (Vds) | 0.57 | 0.54 | 0.54 |
| | ACIDITY INDEX | 0.0 | 10.0 | 10.0 |
| CAPACITANCE COMPONENT (pF) | $C_{40}$ | 68.0 | 88.2 | 79.5 |
| | $C_{100}$ | 64.5 | 75.3 | 74.3 |
| RATE OF CHANGE IN CAPACITANCE COMPONENT (%) | $[(C_{40}-C_{100})/(100-40)]\times 100$ | 5.8 | 21.5 | 8.7 |

It is understood from Table 1 that the acidity measured through use of the pH-ISFET is "0" for the new oil of the sample oil (i) and "10" for the degraded oil (GE) obtained by using the sample oil (ii) in a gasoline engine and the degraded oil (DE) obtained by using the sample oil (iii) used in a diesel engine. Thus, it is understood that there is no substantial difference in degree of degradation between the sample oil (ii) and the sample oil (iii).

On the other hand, the rate (%) of a change in capacitance component (electrostatic capacitance) with respect to a frequency at the frequencies of 40 Hz and 100 Hz is 21.5% for the sample oil (ii) in which a polar substance has been generated due to degradation and a polar substance such as an acidic compound has been simultaneously mixed, and 8.7% for the sample oil (iii) in which a polar substance has been generated due to degradation and soot has been further mixed. Thus, it is considered that the sample oil (ii) corresponds to degraded oil in the degradation state I and the sample oil (iii) corresponds to degraded oil in the degradation state II from the rate of a change in capacitance component (electrostatic capacitance) with respect to a change in frequency, and it is understood that a degradation mechanism (cause of degradation) of a lubricating oil can be predicted therefrom.

Further, it is understood that a degradation mechanism (cause of degradation) of a lubricating oil can be predicted similarly from the difference in the manner of a change in capacitance component (electrostatic capacitance) with respect to two or more frequencies of each sample oil illustrated in FIG. 5.

Comparative Example

The sample oils used in the example were measured for a resistance component (Ω) of a complex impedance with the use of the device for measuring a degree of degradation of a lubricating oil illustrated in FIG. 4. The measuring device, voltage, measurement frequencies, and sample oils that are used are the same as those of the example.

Figure 6:
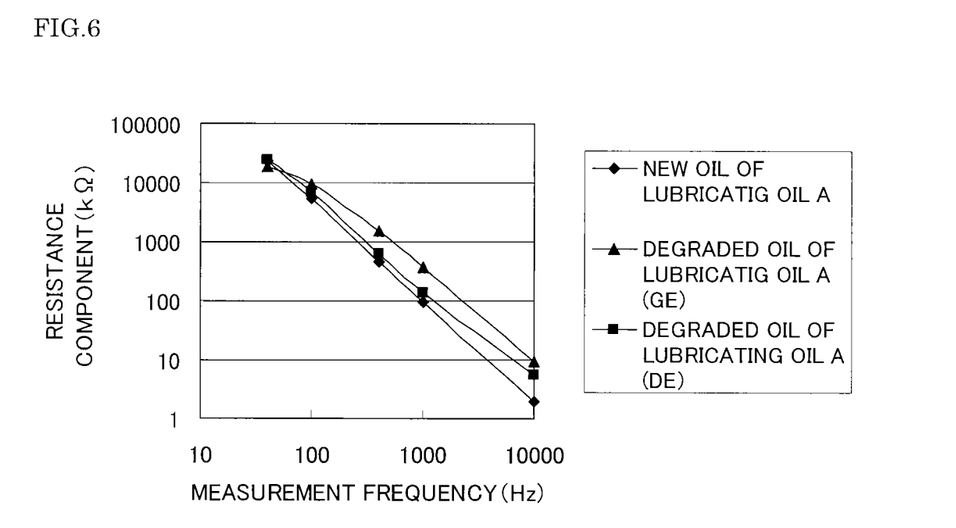
[FIG. 6] A diagram (graph) showing a relationship between the resistance component of a lubricating oil used in a comparative example and the frequency.

FIG. 6 shows the results as a change in resistance component with respect to a frequency. From FIG. 6, no clear difference is recognized in a change in resistance component with respect to a frequency in the new oil as well as the degraded oil of the lubricating oil A of the sample oils (i) to (iii). Thus, it is understood that a degradation mechanism of a lubricating oil cannot be predicted by this method.

Industrial Applicability

According to the present invention, the degree of degradation of a lubricating oil can be measured easily and precisely, and at the same time, the degradation mechanism (cause of degradation) thereof can be predicted. Further, the device for measuring a degree of degradation and transformation of a lubricating oil of the present invention can determine the state of degradation and transformation of even a trace amount of sample oil, and further can be used effectively as a lubrication management system for a machine and a device such as an automobile engine.

The invention claimed is:

1. A method of analyzing a lubricating oil, comprising:
   (a) measuring an acidity of the lubricating oil with an ISFET sensitive to hydrogen ions; and
   (b) measuring a dielectric constant or electrostatic capacitance of the lubricating oil at at least two different frequencies;
   (c) calculating a rate of a change in dielectric constant with respect to the frequency according to the equation $(\epsilon_1-\epsilon_2)/(H_2-H_1)$ or a rate of a change in electrostatic capacitance with respect to the frequency according to the equation $[(C_1-C_2)/(H_2-H_1)]$, wherein
   $H_1$ is a first frequency at which the dielectric constant is measured in (b),
   $H_2$ is a second frequency at which the dielectric constant is measured in (b), and
   $\epsilon_1$ is the dielectric constant measured at $H_1$,
   $\epsilon_2$ is the dielectric constant measured at $H_2$,
   $C_1$ is the electrostatic capacitance measured at $H_1$, and
   $C_2$ is the electrostatic capacitance measured at $H_2$
   and
   (d) determining a cause of degradation of the lubricating oil based on the measured acidity and the value of the calculated rate of change of dielectric constant or the value of the calculated rate of change in electrostatic capacitance.

2. The method of claim 1, further comprising:
   monitoring the measured acidity and determining that the lubricating oil is degraded when the acidity reaches a set value.

3. The method of claim 1, wherein the measuring of the acidity comprises:
   applying a constant voltage between a drain and a source of the ISFET and measuring a current flowing between the drain and the source; or
   applying a constant current to flow between the drain and the source and measuring a voltage between the drain and the source.

4. The method of claim 3, wherein the measuring of the acidity comprises:
   applying different voltages between the drain and the source and measuring a difference of currents between the drain and the source at respective voltage values; or
   applying different currents to flow between the drain and the source and measuring a difference of voltages between the drain and the source at respective current values.

5. The method of claim 1, wherein the first frequency $H_1$ is 100 Hz or less, the second frequency $H_2$ is greater than the first frequency $H_1$, and wherein the second frequency $H_2$ is 10,000 Hz or less.

6. The method of claim 5, wherein $H_1$ is in a range of 5 to 80 Hz.

7. The method of claim 5, wherein $H_1$ is in a range of 10 to 60 Hz.

8. The method of claim 5, wherein $H_2$ is greater than $H_1$ and wherein $H_2$ is 1,000 Hz or less.

9. The method of claim 5, wherein $H_2$ is greater than $H_1$ and wherein $H_2$ is 500 Hz or less.

10. The method of claim 5, wherein $H_2$ is greater than $H_1$ and wherein $H_2$ is 200 Hz or less.

11. A system, comprising:
    a device that analyzes a condition of a lubricating oil, and determines a cause of degradation of the lubricating oil, based on a measured acidity of the lubricating oil, and a rate of change of dielectric constant of the lubricating oil or a rate of change of capacitance of the lubricating oil, comprising:
    (A) an acidity measuring part comprising an ISFET sensitive to hydrogen ions and i) a circuit, which applies a constant voltage between a drain and a source of the ISFET and measures a current flowing between the drain and the source, or ii) a circuit, which applies a constant current to flow between the drain and the source and measures a voltage between the drain and the source, and
    (B) a measuring circuit, which measures either a dielectric constant or an electrostatic capacitance, or both, comprising:
    a pair of electrodes,
    an AC power source, which applies an AC voltage having a frequency of 100 Hz or less between the pair of electrodes and
    a circuit, which calculates a rate of a change in dielectric constant with respect to frequency, or a rate of a change in electrostatic capacitance with respect to frequency, and which analyzes the condition of the lubricating oil and determines the cause of degradation of the lubricating oil, based on the measured acidity and the rate of change in dielectric constant or the rate of change in electrostatic capacitance.

12. The system of claim 11, wherein the device further comprises:
    a dielectric constant calculating part comprising a dielectric constant calculating circuit, which calculates a dielectric constant based on an electrostatic capacitance measured value obtained in the electrostatic capacitance measuring part.

* * * * *